(12) United States Patent
Lee et al.

(10) Patent No.: US 11,951,207 B2
(45) Date of Patent: Apr. 9, 2024

(54) STABLE LIQUID PHARMACEUTICAL PREPARATION

(71) Applicant: Celltrion Inc., Incheon (KR)

(72) Inventors: Joon Won Lee, Incheon (KR); Won Yong Han, Incheon (KR); Su Jung Kim, Incheon (KR); Jun Seok Oh, Incheon (KR); So Young Kim, Incheon (KR); Su Hyeon Hong, Incheon (KR); Yeon Kyeong Shin, Incheon (KR)

(73) Assignee: Celltrion Inc., Incheon (KR)

( * ) Notice: Subject to any disclaimer, the term of this patent is extended or adjusted under 35 U.S.C. 154(b) by 401 days.

(21) Appl. No.: 16/310,585

(22) PCT Filed: Jun. 28, 2017

(86) PCT No.: PCT/KR2017/006855
§ 371 (c)(1),
(2) Date: Dec. 17, 2018

(87) PCT Pub. No.: WO2018/004260
PCT Pub. Date: Jan. 4, 2018

(65) Prior Publication Data
US 2021/0000743 A1 Jan. 7, 2021

(30) Foreign Application Priority Data
Jun. 30, 2016 (KR) .................. 10-2016-0083039

(51) Int. Cl.
| | | |
|---|---|---|
| *A61K 9/08* | (2006.01) | |
| *A61K 39/00* | (2006.01) | |
| *A61K 39/395* | (2006.01) | |
| *A61P 37/02* | (2006.01) | |
| *A61P 37/04* | (2006.01) | |
| *A61P 37/06* | (2006.01) | |
| *C07K 16/00* | (2006.01) | |
| *C07K 16/24* | (2006.01) | |
| *A61K 47/10* | (2017.01) | |
| *A61K 47/18* | (2017.01) | |
| *A61K 47/26* | (2006.01) | |

(52) U.S. Cl.
CPC .............. *A61K 9/08* (2013.01); *A61K 39/00* (2013.01); *A61K 39/395* (2013.01); *A61P 37/02* (2018.01); *A61P 37/04* (2018.01); *A61P 37/06* (2018.01); *C07K 16/00* (2013.01); *C07K 16/241* (2013.01); *A61K 2039/505* (2013.01); *A61K 47/10* (2013.01); *A61K 47/183* (2013.01); *A61K 47/26* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 4,861,335 A | 8/1989 | Reynolds | |
| 5,085,642 A | 2/1992 | Sarnoff et al. | |
| 5,681,291 A | 10/1997 | Galli | |
| 6,284,471 B1 | 9/2001 | Le et al. | |
| 6,331,174 B1 | 12/2001 | Reinhard et al. | |
| 2013/0186797 A1* | 7/2013 | Walsh .................. | A61K 47/183 206/459.5 |
| 2014/0044708 A1 | 2/2014 | Dauty et al. | |
| 2014/0072559 A1 | 3/2014 | Adocia | |
| 2014/0141008 A1 | 5/2014 | Fraunhofer et al. | |
| 2022/0153828 A1 | 5/2022 | Kim | |

FOREIGN PATENT DOCUMENTS

| | | | |
|---|---|---|---|
| CN | 104666242 | 6/2015 | |
| EP | 3085385 A1 | 10/2016 | |
| JP | 2015-519382 | 7/2015 | |
| KR | 102014-0134689 | 11/2014 | |
| UA | 104254 C2 | 1/2014 | |
| WO | 2006044908 A2 | 4/2006 | |
| WO | 2009/155724 A2 | 12/2009 | |
| WO | 2010-129469 | 11/2010 | |
| WO | 2011012637 A2 | 2/2011 | |
| WO | 2013164837 A1 | 3/2013 | |
| WO | WO-2013164837 A1 * | 11/2013 | ............. A61K 47/20 |
| WO | 2013-186230 | 12/2013 | |
| WO | 2014-036071 | 3/2014 | |
| WO | 2014039903 A2 | 3/2014 | |

(Continued)

OTHER PUBLICATIONS

Chang, B.S. and Hershenson, S. 2002. Practical approaches to protein formulation development in "Rationale Design of stable protein formulations-theory and practice" (J.F. Carpenter and M.C. Manning eds.) Kluwer Academic/Plenum publishers, New York. pp. 1-25. (Year: 2002).*
Simponi fact sheet (highlights of prescribing information; downloaded from https://www.accessdata.fda.gov/drugsatfda_docs/label/2016/125289s127lbl.pdf; published Jan. 2016) (Year: 2016).*
Simponi medicine guide revised Jan. 2016.
International Preliminary Report on Patentability and Written Opinion for corresponding PCT Application No. PCT/KR2017/006855 dated Jan. 1, 2019.

(Continued)

*Primary Examiner* — Brian Gangle
*Assistant Examiner* — Andrea K McCollum
(74) *Attorney, Agent, or Firm* — Wood, Phillips, Katz, Clark & Mortimer

(57) ABSTRACT

The present invention provides a stable liquid pharmaceutical formulation containing: an antibody or its antigen-binding fragment; a surfactant; a sugar or its derivative; and a buffer. The stable liquid pharmaceutical formulation according to the present invention has low viscosity while containing a high content of the antibody, has excellent long-term storage stability based on excellent stability under accelerated conditions and severe conditions, and may be administered subcutaneously.

14 Claims, No Drawings
Specification includes a Sequence Listing.

(56) References Cited

FOREIGN PATENT DOCUMENTS

| WO | 2014/058389 | A1 | 4/2014 | | |
|---|---|---|---|---|---|
| WO | 2014/078866 | A2 | 5/2014 | | |
| WO | 2014/114651 | A9 | 7/2014 | | |
| WO | 2015/057910 | A1 | 4/2015 | | |
| WO | 2015/151115 | A1 | 10/2015 | | |
| WO | 2015151115 | | 10/2015 | | |
| WO | 2015177057 | A1 | 11/2015 | | |
| WO | WO-2015177057 | A1 * | 11/2015 | ............ | A61K 47/26 |
| WO | 2016/066688 | A1 | 5/2016 | | |
| WO | 2016/103093 | A1 | 6/2016 | | |
| WO | 2016-128564 | | 8/2016 | | |

OTHER PUBLICATIONS

KIPO Notification of Reason for Refusal for Korean Application No. 10-2017-0081814 dated May 2, 2018.
First Office Action for Taiwan Application No. 106121657 dated Nov. 11, 2018.
Liang, Shuaiyi et al., J Biol Chem. May 10, 2013; 288 (19) : 13799-13807 https://web.archive.org/web/20210513023316/https://www.ncbi.nlm.nih.gov/pmc/articles/PMC3650416/https://www.ncbi.nlm.nih.gov/pmc/articles/PMC3650416/.

* cited by examiner

SEQUENCE LISTING

<160> NUMBER OF SEQ ID NOS: 10

<210> SEQ ID NO 1
<211> LENGTH: 6
<212> TYPE: PRT
<213> ORGANISM: Artificial Sequence
<220> FEATURE:
<223> OTHER INFORMATION: Antibody

<400> SEQUENCE: 1

Gln Phe Val Gly Ser Ser
1               5

<210> SEQ ID NO 2
<211> LENGTH: 3
<212> TYPE: PRT
<213> ORGANISM: Artificial Sequence
<220> FEATURE:
<223> OTHER INFORMATION: Antibody

<400> SEQUENCE: 2

Tyr Ala Ser
1

<210> SEQ ID NO 3
<211> LENGTH: 9
<212> TYPE: PRT
<213> ORGANISM: Artificial Sequence
<220> FEATURE:
<223> OTHER INFORMATION: Antibody

<400> SEQUENCE: 3

Gln Gln Ser His Ser Trp Pro Phe Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Antibody

<400> SEQUENCE: 4

Gly Phe Ile Phe Ser Asn His Trp
1               5

```
<210> SEQ ID NO 5
<211> LENGTH: 10
<212> TYPE: PRT
<213> ORGANISM: Artificial Sequence
<220> FEATURE:
<223> OTHER INFORMATION: Antibody

<400> SEQUENCE: 5

Ile Arg Ser Lys Ser Ile Asn Ser Ala Thr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Antibody

<400> SEQUENCE: 6

Ser Arg Asn Tyr Tyr Gly Ser Thr Tyr Asp Tyr
1               5                   10

<210> SEQ ID NO 7
<211> LENGTH: 107
<212> TYPE: PRT
<213> ORGANISM: Artificial Sequence
<220> FEATURE:
<223> OTHER INFORMATION: Antibody

<400> SEQUENCE: 7

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys
            100                 105

<210> SEQ ID NO 8
<211> LENGTH: 119
<212> TYPE: PRT
<213> ORGANISM: Artificial Sequence
<220> FEATURE:
<223> OTHER INFORMATION: Antibody

<400> SEQUENCE: 8

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
50                  55                  60
```

```
Ser Val Lys Gly Arg Phe Thr Ile Ser Arg Asp Asp Ser Lys Ser Ala
 65                  70                  75                  80

Val Tyr Leu Gln Met Thr Asp Leu Arg Thr Glu Asp Thr Gly Val Tyr
                 85                  90                  95

Tyr Cys Ser Arg Asn Tyr Tyr Gly Ser Thr Tyr Asp Tyr Trp Gly Gln
                100                 105                 110

Gly Thr Thr Leu Thr Val Ser
            115
```

<210> SEQ ID NO 9
<211> LENGTH: 214
<212> TYPE: PRT
<213> ORGANISM: Artificial Sequence
<220> FEATURE:
<223> OTHER INFORMATION: Antibody

<400> SEQUENCE: 9

```
Asp Ile Leu Leu Thr Gln Ser Pro Ala Ile Leu Ser Val Ser Pro Gly
  1               5                  10                  15

Glu Arg Val Ser Phe Ser Cys Arg Ala Ser Gln Phe Val Gly Ser Ser
                 20                  25                  30

Ile His Trp Tyr Gln Gln Arg Thr Asn Gly Ser Pro Arg Leu Leu Ile
             35                  40                  45

Lys Tyr Ala Ser Glu Ser Met Ser Gly Ile Pro Ser Arg Phe Ser Gly
 50                  55                  60

Ser Gly Ser Gly Thr Asp Phe Thr Leu Ser Ile Asn Thr Val Glu Ser
 65                  70                  75                  80

Glu Asp Ile Ala Asp Tyr Tyr Cys Gln Gln Ser His Ser Trp Pro Phe
                 85                  90                  95

Thr Phe Gly Ser Gly Thr Asn Leu Glu Val Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 10
<211> LENGTH: 450
<212> TYPE: PRT
<213> ORGANISM: Artificial Sequence
<220> FEATURE:
<223> OTHER INFORMATION: Antibody

<400> SEQUENCE: 10

```
Glu Val Lys Leu Glu Glu Ser Gly Gly Gly Leu Val Gln Pro Gly Gly
  1               5                  10                  15

Ser Met Lys Leu Ser Cys Val Ala Ser Gly Phe Ile Phe Ser Asn His
                 20                  25                  30
```

```
Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450
```

STABLE LIQUID PHARMACEUTICAL PREPARATION

Incorporated by reference herein is the ASCII plain file text named "Sequence Listing (Corrected)", filed with the United States Patent and Trademark Office on Nov. 20, 2023 which is the creation date thereof, equal to 8,778 bytes.

FIELD OF THE INVENTION

The present invention relates to a stable liquid pharmaceutical formulation.

DESCRIPTION OF THE RELATED ART

Tumor necrosis factor-α (TNF-α) is a cell signaling protein (cytokine) that is involved in systemic inflammation and is a cytokine that mediates acute-phase responses. TNF-α is related to various diseases and disorders, including septicemia, infection, autoimmune diseases, and graft rejection. TNF-α stimulates immune responses and causes many clinical problems associated with autoimmune abnormalities such as rheumatoid arthritis, ankylosing spondylitis, ulcerative colitis, adult Crohn's disease, pediatric Crohn's disease, psoriasis, psoriatic arthritis and the like. Such abnormalities may be treated using TNF-α inhibitors.

Infliximab is a kind of chimeric monoclonal antibody that can function as a TNF-α inhibitor. Conventional formulations containing this antibody are prepared as freeze-dried powders, which are reconstituted, diluted, and injected intravenously using a dosage regimen determined according to each disease.

For example, the REMICADE® (infliximab) label discloses a freeze-dried formulation containing infliximab, sucrose, polysorbate 80 and sodium phosphate. For intravenous injection, it discloses a reconstitution step of adding injectable water to the freeze-dried formulation, and a step of diluting the reconstituted formulation with injectable saline containing sodium chloride.

However, the mode of administration of the conventional formulation as described above (freeze drying→reconstitution→dilution→intravenous administration) has problems in that it is costly, complicated, and causes patient's discomfort due to frequent administration, rejection, and side effects, and in that a person who administers the formulation is limited to a medically trained person.

Adalimumab is also a kind of human monoclonal antibody that can function as a TNF-α inhibitor. A liquid formulation containing adalimumab is disclosed in, for example, the Humira label. Furthermore, Korean Patent Application Publication No. 10-2014-0134689 discloses a liquid formulation containing adalimumab, sodium phosphate, sodium citrate, citric acid, mannitol, sodium chloride, and polysorbate 80 (Example 1), and an improved liquid formulation containing adalimumab, sodium phosphate, sodium citrate, citric acid, mannitol, arginine, sodium chloride, and polysorbate 80 (Example 2).

However, in the case of the above-described liquid pharmaceutical formulations containing NaCl or KCl as an isotonic agent, problems such as precipitation and gelatinization may arise, and when the antibody concentration is as low as about 50 mg/ml, the administration frequency and the administration cycle may be limited.

Accordingly, there is a need for a stable liquid pharmaceutical formulation that can overcome the problems of the above-described conventional liquid pharmaceutical formulations and that contains an antibody, particularly infliximab, as a TNF-α inhibitor.

DISCLOSURE

Technical Problem

It is an object of the present invention to provide a stable liquid pharmaceutical formulation having low viscosity while containing a high content of an antibody.

Another object of the present invention is to provide a liquid pharmaceutical formulation having excellent long-term storage stability based on excellent stability under accelerated conditions and severe conditions.

Still another object of the present invention is to provide a stable liquid pharmaceutical formulation that may be administered subcutaneously.

Technical Solution

A stable liquid pharmaceutical formulation according to one embodiment of the present invention contains: (A) an antibody or its antigen-binding fragment; (B) a surfactant; (C) a sugar or its derivative; and (D) a buffer.

In one embodiment of the present invention, the antibody (A) may comprise an antibody that binds to TNF-α.

In one embodiment of the present invention, the antibody (A) may comprise infliximab, adalimumab, certolizumab pegol, golimumab, or a mixture thereof.

In one embodiment of the present invention, the antibody (A) may comprise a chimeric human-mouse IgG monoclonal antibody.

In one embodiment of the present invention, the antibody or its antigen-binding fragment (A) may comprise: a light-chain variable region comprising a CDR1 domain comprising an amino acid sequence of SEQ ID NO: 1, a CDR2 domain comprising an amino acid sequence of SEQ ID NO: 2, and a CDR3 domain comprising an amino acid sequence of SEQ ID NO: 3; and a heavy-chain variable region comprising a CDR1 domain comprising an amino acid sequence of SEQ ID NO: 4, a CDR2 domain comprising an amino acid sequence of SEQ ID NO: 5, and a CDR3 domain comprising an amino acid sequence of SEQ ID NO: 6.

In one embodiment of the present invention, the antibody or its antigen-binding fragment (A) may comprise: a light-chain variable region having an amino acid sequence of SEQ ID NO: 7; and a heavy-chain variable region having an amino acid sequence of SEQ ID NO: 8.

In one embodiment of the present invention, the antibody (A) may comprise: a light chain having an amino acid sequence of SEQ ID NO: 9; and a heavy chain having an amino acid sequence of SEQ ID NO: 10.

In one embodiment of the present invention, the antibody or its antigen-binding fragment (A) may be contained at a concentration of 10 to 200 mg/ml.

In one embodiment of the present invention, the surfactant (B) may comprise polysorbate, poloxamer, or a mixture thereof.

In one embodiment of the present invention, the surfactant (B) may comprise polysorbate 20, polysorbate 40, polysorbate 60, polysorbate 80, or a mixture of two or more thereof.

In one embodiment of the present invention, the surfactant (B) may comprise polysorbate 80.

In one embodiment of the present invention, the surfactant (B) may be contained at a concentration of 0.02 to 0.1% (w/v).

In one embodiment of the present invention, the sugar (C) may comprise a monosaccharide, a disaccharide, an oligosaccharide, a polysaccharide, or a mixture of two or more thereof, and the sugar derivative (C) may comprise sugar alcohol, sugar acid, or a mixture thereof.

In one embodiment of the present invention, the sugar or its derivative (C) may comprise sorbitol, mannitol, trehalose, sucrose, or a mixture of two or more thereof.

In one embodiment of the present invention, the sugar or its derivative (C) may be contained at a concentration of 1 to 10% (w/v).

In one embodiment of the present invention, the buffer (D) may comprise acetate or histidine.

In one embodiment of the present invention, the buffer (D) may have a concentration of 1 to 50 mM.

In one embodiment of the present invention, the formulation may have a pH of 4.0 to 5.5.

In one embodiment of the present invention, the formulation may be free of aspartic acid, lysine, arginine, or mixtures thereof.

In one embodiment of the present invention, the formulation may be free of NaCl, KCl, NaF, KBr, NaBr, $Na_2SO_4$, NaSCN, $K_2SO_4$, or mixtures thereof.

In one embodiment of the present invention, the formulation may be free of a chelating agent.

In one embodiment of the present invention, the formulation may have a viscosity of 0.5 cp to 10 cp as measured after 1 month of storage at 40° C.±2° C., or a viscosity of 0.5 cp to 5 cp as measured after 6 months of storage at 5° C.±3° C.

A stable liquid pharmaceutical formulation according to one embodiment of the present invention may contain: (A) an antibody or its antigen-binding fragment, which comprises a light-chain variable region comprising a CDR1 domain comprising an amino acid sequence of SEQ ID NO: 1, a CDR2 domain comprising an amino acid sequence of SEQ ID NO: 2, and a CDR3 domain comprising an amino acid sequence of SEQ ID NO: 3; and a heavy-chain variable region comprising a CDR1 domain comprising an amino acid sequence of SEQ ID NO: 4, a CDR2 domain comprising an amino acid sequence of SEQ ID NO: 5, and a CDR3 domain comprising an amino acid sequence of SEQ ID NO: 6; (B) a surfactant; (C) a sugar or its derivative; and (D) a buffer comprising acetate or histidine.

A stable liquid pharmaceutical formulation according to one embodiment of the present invention may contain: (A) 90 to 145 mg/ml of an antibody or its antigen-binding fragment, which comprises a light-chain variable region comprising a CDR1 domain comprising an amino acid sequence of SEQ ID NO: 1, a CDR2 domain comprising an amino acid sequence of SEQ ID NO: 2, and a CDR3 domain comprising an amino acid sequence of SEQ ID NO: 3; and a heavy-chain variable region comprising a CDR1 domain comprising an amino acid sequence of SEQ ID NO: 4, a CDR2 domain comprising an amino acid sequence of SEQ ID NO: 5, and a CDR3 domain comprising an amino acid sequence of SEQ ID NO: 6; (B) 0.02 to 0.1% (w/v) of a surfactant; (C) 1 to 10% (w/v) of a sugar or its derivative; and (D) 1 to 50 mM of a buffer comprising acetate or histidine.

In one embodiment of the present invention, the stable liquid pharmaceutical formulation may be for subcutaneous administration.

In one embodiment of the present invention, the stable liquid pharmaceutical formulation may not be subjected to a reconstitution step, a dilution step, or both, before use.

A pre-filled syringe according to one embodiment of the present invention is filled with the stable liquid pharmaceutical formulation.

An auto-injector according to one embodiment of the present invention includes the pre-filled syringe therein.

Advantages Effects

The stable liquid pharmaceutical formulation according to the present invention has low viscosity while containing a high content of an antibody, has excellent long-term storage stability based on excellent stability under accelerated conditions and severe conditions, and may be administered subcutaneously.

DESCRIPTION OF SPECIFIC EMBODIMENTS

Stable Liquid Pharmaceutical Formulation

A stable liquid pharmaceutical formulation according to the present invention contains: (A) an antibody or its antigen-binding fragment; (B) a surfactant; (C) a sugar or its derivative; and (D) a buffer.

As used herein, the term "free of" means that the formulation is completely free of the corresponding component. In addition, the term means that the formulation is substantially free of the corresponding component, that is, contains the corresponding component in an amount that does not affect the activity of the antibody and the stability and viscosity of the liquid pharmaceutical formulation. For example, the term means that the formulation contains the corresponding component in an amount of 0 to 1% (w/v), 0 to 1 ppm (w/v), or 0 to 1 ppb (w/v), based on the total weight of the liquid pharmaceutical formulation.

(A) Antibody or its Antigen-Binding Fragment

The term "antibody" refers to immunoglobulin molecules comprised of four polypeptide chains, two heavy chains and two light chains inter-connected by disulfide bonds. Other naturally occurring antibodies having an altered structure, for example, camelid antibodies, are also included in this definition. Each heavy chain is comprised of a heavy-chain variable region and a heavy-chain constant region. The heavy-chain constant region is comprised of three domains (CH1, CH2 and CH3). Each light chain is comprised of a light-chain variable region and a light-chain constant region. The light-chain constant region is comprised of one domain (CL). The heavy-chain variable region and the light-chain variable region can be further subdivided into regions of hypervariability, termed complementarity determining regions (CDR), interspersed with regions that are more conserved, termed framework regions (FR). Each of the heavy-chain variable region and the light-chain variable region is composed of three CDRs and four FRs, which are arranged from amino-terminus to carboxy-terminus in the following order: FR1, CDR1, FR2, CDR2, FR3, CDR3, FR4.

In one embodiment of the present invention, the pharmaceutical formulation may contain, as the antibody, a polyclonal antibody, a monoclonal antibody, a recombinant antibody, a single-chain antibody, a hybrid antibody, a chimeric antibody, a humanized antibody, or a fragment thereof. The term "chimeric antibody" refers to an antibody comprising heavy-chain and light-chain variable region sequences from one species and constant region sequences from another species. In one embodiment of the present invention, the pharmaceutical formulation may contain, as the antibody, a chimeric human-mouse IgG monoclonal antibody. The chimeric human-mouse IgG monoclonal antibody is comprised of mouse heavy-chain and light-chain variable regions and human heavy-chain and light-chain constant regions bound thereto. The chimeric human-mouse IgG monoclonal antibody may be produced according to a method known in the art. For example, infliximab may be produced according to a method described in U.S. Pat. No. 6,284,471.

In one embodiment of the present invention, the pharmaceutical formulation may contain, as the antibody, an antibody that binds to TNF-α or the epitope of TNF-α. The antibody that binds to TNF-α or the epitope of TNF-α may comprise infliximab, adalimumab, certolizumab pegol, golimumab, or a mixture thereof. In one embodiment of the present invention, the antibody may comprise infliximab.

In one embodiment of the present invention, the antibody or its antigen-binding fragment (A) may comprise: a light-chain variable region comprising a CDR1 domain comprising an amino acid sequence of SEQ ID NO: 1, a CDR2 domain comprising an amino acid sequence of SEQ ID NO: 2, and a CDR3 domain comprising an amino acid sequence of SEQ ID NO: 3; and a heavy-chain variable region comprising a CDR1 domain comprising an amino acid sequence of SEQ ID NO: 4, a CDR2 domain comprising an amino acid sequence of SEQ ID NO: 5, and a CDR3 domain comprising an amino acid sequence of SEQ ID NO: 6.

In one embodiment of the present invention, the antibody or its antigen binding fragment (A) may comprise: a light-chain variable region having an amino acid sequence of SEQ ID NO: 7; and a heavy-chain variable region having an amino acid sequence of SEQ ID NO: 8.

In one embodiment of the present invention, the antibody or its antigen binding fragment (A) may comprise: a light chain having an amino acid sequence of SEQ ID NO: 9; and a heavy chain having an amino acid sequence of SEQ ID NO: 10.

The concentration of the antibody or its antigen-binding fragment may be freely controlled within a range that does not substantially adversely affect the stability and viscosity of the stable liquid pharmaceutical formulation according to the present invention. In one embodiment of the present invention, the concentration of the antibody or its antigen-binding fragment may be 10 to 200 mg/ml. In another embodiment of the present invention, the concentration of the antibody or its antigen-binding fragment may be 50 to 200 mg/ml. In still another embodiment of the present invention, the concentration of the antibody or its antigen-binding fragment may be 80 to 150 mg/ml. In still another embodiment of the present invention, the concentration of the antibody or its antigen-binding fragment may be 90 to 145 mg/ml. In yet another embodiment of the present invention, the concentration of the antibody or its antigen-binding fragment may be 110 to 130 mg/ml. If the concentration of the antibody or its antigen-binding fragment is within the above-described range, the high content of the antibody or its antigen-binding fragment makes it possible to increase the degree of freedom of dose and administration cycle, and the pharmaceutical formulation may exhibit excellent long-term stability and low viscosity.

(B) Surfactant

Examples of the surfactant include, but are not limited to, polyoxyethylene sorbitan fatty acid ester (e.g., polysorbate), polyoxyethylene alkyl ether (e.g., BRIJ®), alkylphenyl polyoxyethylene ether (e.g., TRITON®-X), polyoxyethylene-polyoxypropylene copolymers (e.g., Poloxamer, PLURONIC®), sodium dodecyl sulfacte (SDS), and the like.

In one embodiment of the present invention, the surfactant may comprise polyoxyethylene sorbitan fatty acid ester (polysorbate). The polysorbate may comprise polysorbate 20, polysorbate 40, polysorbate 60, polysorbate 80, or a mixture of two or more thereof. In one embodiment of the present invention, the polysorbate may comprise polysorbate 20, polysorbate 80, or a mixture thereof. In another embodiment of the present invention, the polysorbate may comprise polysorbate 80.

In one embodiment of the present invention, the concentration of the surfactant may be freely controlled within a range that does not substantially adversely affect the stability and viscosity of the stable liquid pharmaceutical formulation according to the present invention. For example, the concentration of the surfactant may be 0.001 to 5% (w/v), 0.01 to 1% (w/v), or 0.02 to 0.1% (w/v). If the concentration of the surfactant is within the above-described range, the pharmaceutical composition may exhibit excellent long-term stability and low viscosity.

(C) Sugar or its Derivative

The sugar may comprise a monosaccharide, a disaccharide, an oligosaccharide, a polysaccharide, or a mixture of two or more thereof. Examples of the monosacchride include, but are not limited to, glucose, fructose, galactose, and the like. Examples of the disaccharide include, but are not limited to, sucrose, lactose, maltose, trehalose, and the like. Examples of the oligosaccharide include, but are not limited to, fructooligosaccaharides, galactooligosaccaharides, mannanoligosaccaharides, and the like. Examples of the polysaccharide include, but are not limited to, starch, glycogen, cellulose, chitin, pectin, and the like.

The sugar derivative may comprise sugar alcohol, sugar acid, or a mixture thereof. Examples of the sugar alcohol include, but are not limited to, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol, polyglycitol, and the like. Examples of the sugar acid include, but are not limited to, aldonic acid (glyceric acid, etc.), ulosonic acid (neuraminic acid, etc.), uronic acid (glucuronic acid, etc.), aldaric acid (tartaric acid, etc.), and the like.

In one embodiment of the present invention, the sugar or its derivative (C) may comprise sorbitol, mannitol, trehalose, sucrose, or a mixture of two or more thereof.

In one embodiment of the present invention, the concentration of the sugar or its derivative may be freely controlled within a range that does not substantially adversely affect the stability and viscosity of the stable liquid pharmaceutical formulation according to the present invention. For example, the concentration of the sugar or its derivative may be 0.1 to 30% (w/v), 1 to 20% (w/v), or 1 to 10% (w/v). If the concentration of the sugar or its derivative may be within this range, the pharmaceutical composition may exhibit excellent long-term stability and low viscosity.

(D) Buffer

The buffer that is used in the present invention is a neutralizing substance that minimizes the change in pH caused by acid or alkali. Examples of the buffer include phosphate, acetate, succinate, gluconate, glutamate, citrate, histidine, and the like. In one embodiment of the present invention, the buffer may comprise acetate or histidine. If the buffer comprises both acetate and histidine, the stability of the pharmaceutical formulation may be reduced.

In one embodiment of the present invention, the buffer may comprise acetate. Examples of the acetate include, but are not limited to, sodium acetate, zinc acetate, aluminum acetate, ammonium acetate, potassium acetate, and the like. For pH adjustment, the buffer may further comprise an acid, for example, acetic acid. When the buffer comprises acetate, it may be most preferable in terms of pH adjustment and stability.

In one embodiment of the present invention, the buffer may comprise histidine. When the buffer comprises histidine, it may comprise a histidine salt, for example, histidine chloride, histidine acetate, histidine phosphate, histidine sulfate, or the like. For pH adjustment, the buffer may comprise an acid, for example, hydrochloric acid, acetic acid, phosphoric acid, sulfuric acid, or the like.

In one embodiment of the present invention, the stable liquid pharmaceutical formulation may be free of citrate, phosphate, or a mixture thereof.

In one embodiment of the present invention, the concentration of the buffer (or the anion of the buffer) may be freely controlled within a range that does not substantially adversely affect the stability and viscosity of the stable liquid pharmaceutical formulation according to the present invention. For example, the concentration of the buffer or its anion may be 1 to 50 mM, 5 to 30 mM, or 10 to 25 mM. If the concentration of the buffer or its anion is within this range, the pharmaceutical composition may exhibit excellent long-term stability and low viscosity.

(E) pH

In one embodiment of the present invention, the pH of the stable liquid pharmaceutical composition may be 4.0 to 5.5, or 4.7 to 5.3. If the pH is within this range, the pharmaceutical composition may exhibit excellent long-term stability and low viscosity. The pH of the pharmaceutical formulation may be adjusted using the buffer. In other words, if the pharmaceutical formulation contains a certain content of the buffer, it may exhibit the pH in the above-described range without having to use a separate pH-adjusting agent. If citrate, phosphate or a mixture thereof is used as the buffer, it may be difficult to show the pH in the above-described range. If the pharmaceutical formulation further contains an acid (e.g., hydrochloric acid) or a base (e.g., sodium hydroxide) as a separate pH-adjusting agent, the stability of the antibody may be reduced.

(F) Other Components

In one embodiment of the present invention, the stable liquid pharmaceutical formulation may be free of aspartic acid, lysine, arginine, or mixtures thereof. If the stable liquid pharmaceutical formulation contains these amino acids, it may become solid. In one embodiment of the present invention, the stable liquid pharmaceutical formulation may contain one or more amino acids, excluding the above-described three amino acids. In this case, the stable liquid pharmaceutical formulation may contain the one or more amino acid in an amount of 5% (w/v) or less, for example, 0.001 to 5% (w/v), 0.001 to 1% (w/v), 0.01 to 5% (w/v), 0.01 to 1% (w/v), 0.1 to 5% (w/v), or 0.1 to 1% (w/v).

In another embodiment of the present invention, the stable liquid pharmaceutical formulation may contain taurine. In this case, the taurine may be contained in an amount of 5% (w/v) or less, for example, 0.001 to 5% (w/v), 0.001 to 1% (w/v), 0.01 to 5% (w/v), 0.01 to 1% (w/v), 0.1 to 5% (w/v), or 0.1 to 1% (w/v).

In one embodiment of the present invention, the stable liquid pharmaceutical formulation may be free of a metal salt, such as NaCl, KCl, NaF, KBr, NaBr, $Na_2SO_4$, NaSCN, $K_2SO_4$ or the like. If the stable liquid pharmaceutical formulation contains these metal salts, precipitation in the formulation may occur, and the formulation may be gelatinized and may have poor stability.

In one embodiment of the present invention, the stable liquid pharmaceutical formulation may be free of a chelating agent (e.g., EDTA (Ethylenediaminetetraacetic acid)). If the pharmaceutical formulation contains a chelating agent, the oxidation rate thereof may be increased.

In one embodiment of the present invention, the stable liquid pharmaceutical formulation may be free of a preservative. Examples of the preservative include octadecyl dimethylbenzyl ammonium chloride, hexamethonium chloride, benzalkonium chloride, benzethonium chloride, phenol, butyl alcohol, benzyl alcohol, alkyl paraben, catechol, resorcinol, cyclohexanol, 3-pentanol, m-cresol, and the like. If the pharmaceutical formulation contains the preservative, the preservative may not help improve the stability of the pharmaceutical formulation.

In one embodiment of the present invention, the stable liquid pharmaceutical formulation of the present invention may further contain an additive known in the art, which does not substantially adversely affect the activity of the antibody and the stability and low viscosity of the formulation. For example, the pharmaceutical formulation may further contain an aqueous carrier, an antioxidant, or a mixture of two or more thereof. The aqueous carrier is a carrier that is pharmaceutically acceptable (safe and non-toxic when administered to humans) and is useful for preparation of liquid pharmaceutical formulations. Examples of the aqueous carrier include, but are not limited to, sterile water for injection (SWFI), bacteriostatic water for injection (BWFI), sterile saline solution, Ringer's solution, dextrose, and the like. Examples of the antioxidant include, but are not limited to, ascorbic acid and the like.

(G) "Stable" Liquid Pharmaceutical Formulation

The term "stable" in the "stable" liquid pharmaceutical formulation of the present invention means that the antibody according to the present invention essentially retains its physical stability and/or chemical stability and/or biological activity during production and/or upon storage. Various analytical techniques for measuring protein stability are readily available in the art.

Physical stability may be assessed by methods known in the art, which include measurement of a sample's apparent attenuation of light (absorbance, or optical density). Such a measurement of light attenuation is related to the turbidity of a formulation. In addition, for physical stability, the contents of high-molecular-weight components, the contents of low-molecular-weight components, the amounts of intact proteins, the number of sub-visible particles, and the like, may be measured.

Chemical stability can be assessed by, for example, detecting and quantifying chemically altered forms of the antibody. Chemical stability includes charge alteration (for example, occurring as a result of deamidation or oxidation) which can be evaluated by, for example, ion-exchange chromatography. For chemical stability, charge variants (acidic or basic peaks) may be measured.

Biological activity may be assessed by methods known in the art. For example, antigen binding affinity may be measured by ELISA.

In one embodiment of the present invention, the liquid pharmaceutical formulation may be stable for a long period of time.

In one embodiment of the present invention, the term "stable" liquid pharmaceutical formulation means a liquid pharmaceutical formulation satisfying one or more of the following criteria.

Turbidity
- a liquid pharmaceutical formulation having an absorbance A600 of 0 to 0.0300, or 0 to 0.0700, as measured by a spectrophotometer after 4 weeks of storage at a temperature of 40° C.±2° C.;
- a liquid pharmaceutical formulation having an absorbance A600 of 0 to 0.0300, or 0 to 0.0700, as measured by a spectrophotometer after 4 weeks of storage at a temperature of 40° C.±2° C. and a relative humidity of 75±5% under a closed condition;

Content of Main Component (main peak)
- a liquid pharmaceutical formulation in which the content of a main component content after 4 weeks of storage at a temperature of 40° C.±2° C. is 98% to 100% as measured by SE-HPLC;
- a liquid pharmaceutical formulation in which the content of a main component content after 4 weeks of storage at a temperature of 40° C.±2° C. and a relative humidity of 75±5% under a closed condition is 98% to 100% as measured by SE-HPLC;

Content of High-Molecular-Weight Components (a peak whose retention time is earlier than that of the main peak (intact IgG))
- a liquid pharmaceutical formulation in which the content of high-molecular-weight components after 12 months of storage at a temperature of 5° C.±3° C. is 0 to 1.00% as measured by SE-HPLC;
- a liquid pharmaceutical formulation in which the content of high-molecular-weight components after 12 months of storage at a temperature of 5° C.±3° C. under a closed condition is 0 to 1.00% as measured by SE-HPLC;

Content of Low-Molecular-Weight Components (a peak whose retention time is later than that of the main peak (intact IgG)
- a liquid pharmaceutical formulation in which the content of low-molecular-weight components after 12 months of storage at a temperature of 5° C.±3° C. is 0 to 0.40% as measured by SE-HPLC;
- a liquid pharmaceutical formulation in which the content of low-molecular-weight components after 12 months of storage at a temperature of 5° C.±3° C. under a closed condition is 0 to 0.40% as measured by SE-HPLC;

Content of Intact Immunoglobulin G
- a liquid pharmaceutical formulation in which the content of intact immunoglobulin G (intact IgG %) after 12 months of storage at a temperature of 5° C.±3° C. is 94.0% to 100% as measured by non-reduced CE-SDS;
- a liquid pharmaceutical formulation in which the content of intact immunoglobulin G (intact IgG %) after 12 months of storage at a temperature of 5° C.±3° C. under a closed condition is 94.0% to 100% as measured by non-reduced CE-SDS;
- a liquid pharmaceutical formulation in which the content of intact immunoglobulin G (intact IgG %) after 4 weeks of storage at a temperature of 40° C.±2° C. is 94.0% to 100% as measured by non-reduced CE-SDS;
- a liquid pharmaceutical formulation in which the content of intact immunoglobulin G content (intact IgG %) after 4 weeks of storage at a temperature of 40° C.±2° C. and a relative humidity of 75±5% under a closed condition is 94.0% to 100% as measured by non-reduced CE-SDS;

Content of Intact Heavy Chain and Light Chain
- a liquid pharmaceutical formulation in which the content of intact heavy chain and light chain (intact HC+LC %) after 12 months of storage at a temperature of 5° C.±3° C. is 99.0% to 100% as measured by reduced CE-SDS;
- a liquid pharmaceutical formulation in which the content of intact heavy chain and light chain (intact HC+LC %) after 12 months of storage at a temperature of 5° C.±3° C. under a closed condition is 99.0% to 100% as measured by reduced CE-SDS;
- a liquid pharmaceutical formulation in which the content of intact heavy chain and light chain (intact HC+LC %) after 4 weeks of storage at a temperature of 40° C.±2° C. is 98.0% to 100% as measured by reduced CE-SDS;
- a liquid pharmaceutical formulation in which the content of intact heavy chain and light chain content (intact HC+LC %) after 4 weeks of storage at a temperature of 40° C.±2° C. under a closed condition is 98.0% to 100% as measured by reduced CE-SDS;

Number of Sub-Visible Particles
- a liquid pharmaceutical formulation in which the number of sub-visible particles (≥10.00 μm, <400.00 μm) after 12 months of storage at a temperature of 5° C.±3° C. is 0 to 1,000 as measured by HIAC;
- a liquid pharmaceutical formulation in which the number of sub-visible particles (≥10.00 μm, <400.00 μm) after 12 months of storage at a temperature of 5° C.±3° C. under a closed condition is 0 to 1,000 as measured by HIAC;
- a liquid pharmaceutical formulation in which the number of sub-visible particles (≥1.00 μm, <100.00 μm) after 4 weeks of storage at a temperature of 40° C.±2° C. is 0 to 30,000 as measured by MFI;
- a liquid pharmaceutical formulation in which the number of sub-visible particles (≥1.00 μm, <100.00 μm) after 4 weeks of storage at a temperature of 40° C.±2° C. and a relative humidity of 75±5% under a closed condition is 0 to 30,000 as measured by MFI;
- a liquid pharmaceutical formulation in which the number of sub-visible particles (≥10.00 μm, <100.00 μm) after 4 weeks of storage at a temperature of 40° C.±2° C. is 0 to 200 as measured by MFI;
- a liquid pharmaceutical formulation in which the number of sub-visible particles (≥10.00 μm, <100.00 μm) after 4 weeks of storage at a temperature of 40° C.±2° C. and a relative humidity of 75±5% under a closed condition is 0 to 200 as measured by MFI;
- a liquid pharmaceutical formulation in which the number of sub-visible particles (≥10.00 μm, <100.00 μm) after 6 weeks of storage at a temperature of 40° C.±2° C. is 0 to 500 as measured by MFI;
- a liquid pharmaceutical formulation in which the number of sub-visible particles (≥10.00 μm, <100.00 μm) after 6 weeks of storage at a temperature of 40° C.±2° C. and a relative humidity of 75±5% under a closed condition is 0 to 500 as measured by MFI;

Oxidation Rate
- a liquid pharmaceutical formulation in which the oxidation rate of heavy-chain Met 255 after 4 weeks of storage at a temperature of 40° C.±2° C. is 0% to 2.5% as measured by LC-MS;
- a liquid pharmaceutical formulation in which the oxidation rate of heavy-chain Met 255 after 4 weeks of storage at a temperature of 40° C.±2° C. and a relative humidity of 75±5% under a closed condition is 0% to 2.5% as measured by LC-MS;

Charge Variants a liquid pharmaceutical formulation showing an acidic peak of 20% to 35% as measured by IEC-HPLC after 4 weeks of storage at a temperature of 40° C.±2° C.;

a liquid pharmaceutical formulation showing an acidic peak of 20% to 35% as measured by IEC-HPLC after 4 weeks of storage at a temperature of 40° C.±2° C. and a relative humidity of 75±5% under a closed condition;

a liquid pharmaceutical formulation showing a basic peak of 33% to 40% as measured by IEC-HPLC after 4 weeks of storage at a temperature of 40° C.±2° C.;

a liquid pharmaceutical formulation showing a basic peak of 33% to 40% as measured by IEC-HPLC after 4 weeks of storage at a temperature of 40° C.±2° C. and a relative humidity of 75±5% under a closed condition;

TNF-α Binding Affinity a liquid pharmaceutical formulation having a TNF-α binding affinity of 80% to 120% as measured by ELISA after 12 months of storage at a temperature of 5° C.±3° C.; and a liquid pharmaceutical formulation having a TNF-α binding affinity of 80% to 120% as measured by ELISA after 12 months of storage at a temperature of 5° C.±3° C. under a closed condition.

In one embodiment of the present invention, the pharmaceutical formulation may have a viscosity of 0.5 cp to 10.0 cp as measured after 1 month of storage at a temperature of 40° C.±2° C. In another embodiment of the present invention, the pharmaceutical formulation may have a viscosity of 0.5 cp to 5.0 cp as measured after 6 months of storage at a temperature of 5° C.±3° C.

Method for Preparation of Stable Liquid Pharmaceutical Formulation

The stable liquid pharmaceutical formulation of the present invention may be prepared using any known method which is not limited to a particular method. For example, the stable liquid pharmaceutical formulation may be prepared by adding a buffer to a solution containing a surfactant and a sugar or its derivative while adjusting the pH of the solution, and then adding an antibody to the mixed solution. Alternatively, the liquid pharmaceutical formulation may be prepared by preparing a solution containing some excipients in the final step of a purification process, and then adding the remaining component to the solution. For example, the liquid pharmaceutical formulation may be prepared by preparing a solution containing an antibody, a buffer and a sugar or its derivative, and then adding a surfactant to the solution.

In addition, the method for preparation of the formulation may comprise or not comprise a freeze-drying step.

When the preparation method does not comprise the freeze-drying step, for example, the liquid pharmaceutical formulation prepared according to the present invention may be treated by sterilization, and then immediately placed in a closed container.

When the preparation method comprises the freeze-drying step, for example, the liquid pharmaceutical formulation prepared according to the present invention may be freeze-dried or freeze-dried and stored, and then components removed or modified by freeze drying and/or storage may be supplemented or replaced, thereby preparing the liquid pharmaceutical formulation according to the present invention. Alternatively, only components of the liquid pharmaceutical formulation of the present invention, excluding components that may be removed or modified by freeze drying and/or storage, may be freeze-dried or freeze-dried and stored, and then the excluded components may be added thereto, thereby preparing the liquid pharmaceutical formulation according to the present invention.

Method of Use of Stable Liquid Pharmaceutical Formulation

The stable liquid pharmaceutical formulation according to the present invention may be used for treating diseases in which the activity of TNF-α acts as a harmful factor. Examples of diseases in which the activity of TNF-α acts as a harmful factor include, but are not limited to, septicemia, autoimmune diseases, infectious diseases, graft rejection, malignant cancer, lung disorders, bowel disorders, heart disorders, and the like.

In one embodiment of the present invention, the diseases in which the activity of TNF-α acts as a harmful factor may be selected from among rheumatoid arthritis, ankylosing spondylitis, ulcerative colitis, adult Crohn's disease, pediatric Crohn's disease, psoriasis, and psoriatic arthritis.

The stable liquid pharmaceutical formulation according to the present invention may be provided as a single-dosage form, a multiple-dosage form, or a form for subcutaneous self-injection.

The concentrations of other components, including the antibody, in the liquid pharmaceutical formulation, are as described above, and the total volume of the liquid pharmaceutical formulation may be 0.2 to 2.0 mL.

The dose and timing of administration of the liquid pharmaceutical formulation may vary depending on the kind of disease, the severity and course of the disease, the patient's health and response to treatment, and the judgment of the treating physician, and is not limited to a particular dose and timing of administration. For example, one or several products containing the liquid pharmaceutical formulation may be administered at a dose of 1 to 10 mg/kg based on the antibody concentration, and then the same or different doses may be administered at intervals of one week, two weeks, three weeks, one month, two months or three months.

In one embodiment of the present invention, the stable liquid pharmaceutical formulation may not be subjected to a reconstitution step, a dilution step, or both, before use.

Treatment Method and Stabilization Method

The present invention also provide a method for treating a patient having a disease in which TNF-α activity acts as a harmful factor, the method comprising administering to the patient a stable liquid pharmaceutical formulation containing: (A) an antibody or its antigen binding fragment; (B) a surfactant; (C) a sugar or its derivative; and (D) a buffer.

The present invention also provides a method of stabilizing an antibody in a liquid pharmaceutical formulation, the method comprising preparing a stable liquid pharmaceutical containing: (A) an antibody or its antigen binding fragment; (B) a surfactant; (C) a sugar or its derivative; and (D) a buffer.

In one embodiment of the treating method or the stabilizing method, the antibody (A) may comprise an antibody that binds to TNF-α.

In one embodiment of the treating method or the stabilizing method, the antibody (A) may comprise infliximab, adalimumab, certolizumab pegol, golimumab, or a mixture thereof.

In one embodiment of the treating method or the stabilizing method, the antibody (A) may comprise a chimeric human-mouse IgG monoclonal antibody.

In one embodiment of the treating method or the stabilizing method, the antibody (A) or its the antigen binding fragment thereof may comprise: a light-chain variable region comprising a CDR1 domain comprising an amino acid sequence of SEQ ID NO: 1, a CDR2 domain comprising an amino acid sequence of SEQ ID NO: 2, and a CDR3 domain comprising an amino acid sequence of SEQ ID NO: 3; and a heavy-chain variable region comprising a CDR1 domain comprising an amino acid sequence of SEQ ID NO: 4, a CDR2 domain comprising an amino acid sequence of SEQ ID NO: 5, and a CDR3 domain comprising an amino acid sequence of SEQ ID NO: 6.

In one embodiment of the treating method or the stabilizing method, the antibody or its antigen binding fragment (A) may comprise: a light-chain variable region having an amino acid sequence of SEQ ID NO: 7; and a heavy-chain variable region having an amino acid sequence of SEQ ID NO: 8.

In one embodiment of the treating method or the stabilizing method, the antibody (A) may comprise: a light chain having an amino acid sequence of SEQ ID NO: 9; and a heavy chain having an amino acid sequence of SEQ ID NO: 10.

In one embodiment of the treating method or the stabilizing method, the antibody or its antigen binding fragment (A) may be contained at a concentration of 10 to 200 mg/ml.

In one embodiment of the treating method or the stabilizing method, the surfactant (B) may comprise polysorbate, poloxamer, or a mixture thereof.

In one embodiment of the treating method or the stabilizing method, the surfactant (B) may comprise polysorbate 20, polysorbate 40, polysorbate 60, polysorbate 80, or a mixture of two or more thereof.

In one embodiment of the treating method or the stabilizing method, the surfactant (B) may comprise polysorbate 80.

In one embodiment of the treating method or the stabilizing method, the surfactant (B) may be contained at a concentration of 0.02 to 0.1% (w/v).

In one embodiment of the treating method or the stabilizing method, the sugar (C) may comprise a monosaccharide, a disaccharide, an oligosaccharide, a polysaccharide, or a mixture of two or more thereof, and the sugar derivative (C) may comprise sugar alcohol, sugar acid, or a mixture thereof.

In one embodiment of the treating method or the stabilizing method, the sugar or its derivative (C) may comprise sorbitol, mannitol, trehalose, sucrose, or a mixture of two or more thereof.

In one embodiment of the treating method or the stabilizing method, the sugar or its derivative (C) may be contained at a concentration of 1 to 10% (w/v).

In one embodiment of the treating method or the stabilizing method, the buffer (D) may comprise acetate or histidine.

In one embodiment of the treating method or the stabilizing method, the buffer (D) may have a concentration of 1 to 50 mM.

In one embodiment of the treating method or the stabilizing method, the stable liquid pharmaceutical formulation may have a pH of 4.0 to 5.5.

In one embodiment of the treating method or the stabilizing method, the stable liquid pharmaceutical formulation may be free of aspartic acid, lysine, arginine, or mixtures thereof.

In one embodiment of the treating method or the stabilizing method, the stable liquid pharmaceutical formulation may be free of NaCl, KCl, NaF, KBr, NaBr, $Na_2SO_4$, NaSCN, $K_2SO_4$, or mixtures thereof.

In one embodiment of the treating method or the stabilizing method, the stable liquid pharmaceutical formulation may be free of a chelating agent.

In one embodiment of the treating method or the stabilizing method, the stable liquid pharmaceutical formulation may be free of a preservative.

In one embodiment of the treating method or the stabilizing method, the stable liquid pharmaceutical formulation may further contain an aqueous carrier, an antioxidant, or a mixture of two or more thereof.

In one embodiment of the treating method or the stabilizing method, the stable liquid pharmaceutical formulation may have a viscosity of 0.5 cp to 10 cp as measured after 1 month of storage at a temperature of 40° C.±2° C., or a viscosity of 0.5 cp to 5 cp as measured after 6 months of storage at a temperature of 5° C.±3° C.

In one embodiment of the treating method or the stabilizing method, the stable liquid pharmaceutical formulation may contain: (A) an antibody or its antigen binding fragment, which comprises a light-chain variable region comprising a CDR1 domain comprising an amino acid sequence of SEQ ID NO: 1, a CDR2 domain comprising an amino acid sequence of SEQ ID NO: 2, and a CDR3 domain comprising an amino acid sequence of SEQ ID NO: 3; and a heavy-chain variable region comprising a CDR1 domain comprising an amino acid sequence of SEQ ID NO: 4, a CDR2 domain comprising an amino acid sequence of SEQ ID NO: 5, and a CDR3 domain comprising an amino acid sequence of SEQ ID NO: 6; (B) a surfactant; (C) a sugar or its derivative; and (D) a buffer comprising acetate or histidine.

In one embodiment of the treating method or the stabilizing method, the stable liquid pharmaceutical formulation may contain: (A) 90 to 145 mg/ml of an antibody or its antigen binding fragment, which comprises a light-chain variable region comprising a CDR1 domain comprising an amino acid sequence of SEQ ID NO: 1, a CDR2 domain comprising an amino acid sequence of SEQ ID NO: 2, and a CDR3 domain comprising an amino acid sequence of SEQ ID NO: 3; and a heavy-chain variable region comprising a CDR1 domain comprising an amino acid sequence of SEQ ID NO: 4, a CDR2 domain comprising an amino acid sequence of SEQ ID NO: 5, and a CDR3 domain comprising an amino acid sequence of SEQ ID NO: 6; (B) 0.02 to 0.1% (w/v) of a surfactant; (C) 1 to 10% (w/v) of a sugar or its derivative; and (D) 1 to 50 mM of a buffer comprising acetate or histidine.

In one embodiment of the treating method, the stable liquid pharmaceutical formulation may be administered subcutaneously.

In one embodiment of the treating method or the stabilizing method, the stable liquid pharmaceutical formulation may not be subjected to a reconstitution step, a dilution step, or both, before use.

In one embodiment of the treating method or the stabilizing method, the stable liquid pharmaceutical formulation may be filled in a pre-filled syringe before use.

In one embodiment of the treating method or the stabilizing method, the pre-filled syringe may be included in an auto-injector before use.

Product

The present invention also provides a product comprising: the stable liquid pharmaceutical formulation; and a container receiving the stable liquid pharmaceutical formulation in a closed state.

The stable liquid pharmaceutical formulation is as described above.

In one embodiment of the present invention, the container may be formed of a material such as glass, a polymer (plastic), a metal or the like, but is not limited thereto. In one embodiment of the present invention, the container is a bottle, a vial, a cartridge, a syringe (pre-filled syringe, auto-syringe), or a tube, but is not limited thereto. In one embodiment of the present invention, the container may be a glass or polymer vial, or a glass or polymer pre-filled syringe.

Specific product forms of the above-described vial, cartridge, pre-filled syringe or auto-syringe, and methods of filling the stabile liquid pharmaceutical formulation into the vial, cartridge, pre-filled syringe or auto-syringe, may be readily available or implemented by any person skilled in the technical field to which the present invention pertains. For example, U.S. Pat. Nos. 4,861,335 and 6,331,174, etc., disclose the specific product form of a pre-filled syringe and a filling method. For example, U.S. Pat. Nos. 5,085,642 and 5,681,291, etc., disclose the specific product form of an auto-syringe and an assembly method. The above-described vial, cartridge, pre-filled syringe or auto-syringe that is used in the present invention may be a commercially available product, or a product separately manufactured considering the physical properties of the stable liquid pharmaceutical formulation, an area to which the formulation is to be administered, the dose of the formulation, and the like.

In one embodiment of the present invention, the inside of the container may not be coated with silicone oil. If it is coated with silicone oil, the stability of the formulation may be reduced. The container may be a single-dose or multiple-dose container.

In one embodiment of the present invention, the product may further comprise instructions providing a method of using the stable liquid pharmaceutical formulation, a method of storing the formulation, or both. The method of using the formulation includes a method for treating a disease in which TNF-α activity acts as a harmful factor, and may include the route of administration, the dose of the formulation, and the timing of administration.

In one embodiment of the present invention, the product may comprise other required utensils (e.g., a needle, a syringe, etc.) in a commercial viewpoint and a user viewpoint.

Hereinafter, the present invention will be described with reference to examples. It is to be understood, however, that these examples are for illustrative purposes only and are not intended to limit the scope of the present invention.

EXAMPLES

The antibody used in the following experimental examples was infliximab purified from commercially available REMSIMA® (manufactured by Celltrion).

The physical stability, chemical stability and biological activity of liquid pharmaceutical formulations used in the following experimental examples were measured using the following methods.

Turbidity
The absorbance at 600 nm was measured using a UV-Vis spectrophotometer.
Content of Main Component
The main component content (main peak %) was measured using size exclusion high-performance liquid chromatography (HPLC).

Content of High-Molecular-Weight Components
The content of high-molecular-weight components (pre-peak %) was measured using size exclusion high-performance liquid chromatography (HPLC).
Content of Low-Molecular-Weight Components
The content of low-molecular-weight components (post-peak %) was measured using size exclusion high-performance liquid chromatography (HPLC).
Content of Intact Immunoglobulin G (intact IgG %)
The content of intact immunoglobulin G (%) was measured using Non-Reduced Capillary Electrophoresis-Sodium Dodecyl Sulfate (NR CE-SDS).
Content of Intact Heavy Chain and Light Chain (intact HC+LC %)
The content of intact heavy chain and light chain (%) was measured using Reduced Capillary Electrophoresis-Sodium Dodecyl Sulfate (R CE-SDS).
Number of Sub-Visible Particles
Experimental Examples 1 to 4: the number of sub-visible particles was measured using Micro Flow Imaging (MFI).
Experimental Example 5: the number of sub-visible particles was measured using a light-shielding liquid particle counter (model: HIAC 9703).
Oxidation
The oxidation (%) of heavy chain Met 255 was measured by peptide mapping using liquid chromatography-mass spectrometry (LC-MS).
Change Variants
Acidic and basic peaks (%) were measured by Ion Exchange Chromatography-High Performance Liquid Chromatography (IEC-HPLC).
TNF-α Binding Affinity
TNF-α binding affinity (%) was measured by Enzyme-Linked ImmunoSorbent Assay (ELISA).
Viscosity
Using a micro-capillary flow system (apparent shear rate: $10^3$ to $10^5$ $s^{-1}$) equipped with a flow cell (B05 sensor type; 50 μm cell depth), viscosity was measured in a 500 μL syringe at 25° C.±0.1° C.

Experimental Example 1

Comparison of Sugar Alcohol with NaCl;
Comparison of Acetate/Histidine Buffer with
Citrate/Phosphate Buffer; Comparison of pH 4-5.5
with pH 6-7

For preparation of liquid pharmaceutical formulations to be used in Experimental Example 1, each buffer was prepared so as to have a desired pH, and sorbitol or NaCl was added thereto. Then, an antibody was added thereto and a surfactant was added, thereby preparing the samples shown in Table 1 below. The specific content of each component is shown in Table 1 below. The concentration of the buffer means the molecular/anion concentration of the corresponding compound. The total volume was 1 ml.

TABLE 1

|  | Antibody content (mg/ml) | Surfactant | Sugar alcohol or NaCl | Buffer | pH |
| --- | --- | --- | --- | --- | --- |
| Example 1 | 100 | Polysorbate 80 0.05% (w/v) | Sorbitol 5%(w/v) | Sodium acetate 10 mM | 4.0 |

TABLE 1-continued

| | Antibody content (mg/ml) | Surfactant | Sugar alcohol or NaCl | Buffer | pH |
|---|---|---|---|---|---|
| Example 2 | 100 | Polysorbate 80 0.05% (w/v) | Sorbitol 5%(w/v) | Histidine 10 mM | 5.5 |
| Example 3 | 100 | Polysorbate 20 0.05%(w/v) | Sorbitol 5%(w/v) | Histidine 10 mM | 5.5 |
| Comparative Example 1 | 100 | Polysorbate 80 0.05%(w/v) | NaCl 140 mM | Sodium acetate 10 mM | 4.0 |
| Comparative Example 2 | 100 | Polysorbate 80 0.05%(w/v) | NaCl 140 mM | Sodium citrate 10 mM | 5.0 |
| Comparative Example 3 | 100 | Polysorbate 80 0.05%(w/v) | Sorbitol 5%(w/v) | Sodium citrate 10 mM | 5.0 |
| Comparative Example 4 | 100 | Polysorbate 80 0.05%(w/v) | NaCl 140 mM | Histidine 10 mM | 5.5 |
| Comparative Example 5 | 100 | Polysorbate 80 0.05%(w/v) | NaCl 140 mM | Sodium phosphate 10 mM | 6.0 |
| Comparative Example 6 | 100 | Polysorbate 80 0.05%(w/v) | Sorbitol 5%(w/v) | Sodium phosphate 10 mM | 6.0 |
| Comparative Example 7 | 100 | Polysorbate 80 0.05%(w/v) | NaCl 140 mM | Sodium phosphate 10 mM | 7.0 |
| Comparative Example 8 | 100 | Polysorbate 80 0.05%(w/v) | Sorbitol 5%(w/v) | Sodium phosphate 10 mM | 7.0 |

Liquid pharmaceutical formulations prepared according to Examples 1 to 3 and Comparative Examples 1 to 8 were stored for 2 weeks at a temperature of 40±2° C. and a relative humidity of 75±5%. As a result, the formulations containing NaCl (Comparative Examples 1, 2, 4, 5 and 7) all showed precipitation and a form like gelatin. In addition, Comparative Example 3, containing sorbitol, but containing sodium citrate, and Comparative Example 8 containing sorbitol, but containing sodium phosphate, also showed a form like gelatin.

Among the formulations containing sorbitol, only the formulations of Examples 1, 2 and 3 and Comparative Example 6 did not show a gelatin form. The formulations were measured for their stability after 0, 2 and 4 weeks of storage at a temperature of 5±3° C. and their stability after 2 and 4 weeks of storage at a temperature of 40±2° C. and a relative humidity of 75±5%. The results of the measurement are shown in Tables 2 to 9 below.

Turbidity

TABLE 2

| | After 0 week at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|
| Example 1 | 0.0082 | 0.0060 | 0.0087 | 0.0364 | 0.0263 |
| Example 2 | 0.0099 | 0.1550 | 0.0082 | 0.0291 | 0.0562 |
| Example 3 | 0.0112 | 0.0059 | 0.0082 | 0.0358 | 0.0643 |
| Comparative Example 6 | 0.0120 | 0.0228 | 0.0138 | 0.1127 | 0.3113 |

As can be seen in Table 2 above, the formulation of Example 1, having a pH of 4 and containing acetate as the buffer, was the best in terms of turbidity, and particularly, showed an absorbance of 0.0300 or lower after 4 weeks of storage at 40° C. Furthermore, it can be seen that the formulations of Example 2 and 3, having a pH of 5.5 and containing histidine as the buffer, also showed an absorbance of 0.0700 or lower after 4 weeks of storage at 40° C. However, it can be seen that the formulation of Comparative Example 6, having a pH of 6 and containing phosphate as the buffer, showed significantly increased turbidity after 2 and 4 weeks of storage at 40° C.

Content of High-Molecular-Weight Components

TABLE 3

| | After 0 week at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|
| Example 1 | 0.4 | 0.8 | 0.6 | 0.8 | 0.7 |
| Example 2 | 0.6 | 1.1 | 0.9 | 1.6 | 1.4 |
| Example 3 | 0.6 | 1.1 | 0.8 | 1.4 | 1.3 |
| Comparative Example 6 | 0.8 | 1.5 | 1.2 | 2.4 | 2.3 |

As can be seen in Table 3 above, the formulation of Example 1 showed the lowest high-molecular-weight component content under all the conditions. Particularly, the formulation of Example 1 showed a high-molecular-weight component content of 1.0% or less after 4 weeks of storage at a temperature of 40° C. Furthermore, it can be seen that the formulations of Examples 2 and 3 showed a high-molecular-weight component content of 1.5% or less after 4 weeks of storage at a temperature of 40° C.

Content of Intact Immunoglobulin G (Intact IgG %)

TABLE 4

| | After 0 week at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|
| Example 1 | 97.7 | 98.8 | 98.0 | 96.9 | 94.5 |
| Example 2 | 97.4 | 98.7 | 98.2 | 97.4 | 94.6 |
| Example 3 | 97.2 | 98.9 | 97.8 | 97.4 | 94.4 |
| Comparative Example 6 | 97.2 | 98.6 | 98.3 | 97.1 | 93.6 |

As can be seen in Table 4 above, the contents of intact immunoglobulin in the formulations of Examples 1 to 3 after 4 weeks of storage at a temperature of 40° C. were 94.0% or more, which was higher than that of Comparative Example 6.

Content of Intact Heavy Chain and Light Chain (Intact HC+LC %)

TABLE 5

| | After 0 week at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|
| Example 1 | 99.5 | 99.6 | 99.5 | 99.2 | 98.3 |
| Example 2 | 99.5 | 99.6 | 99.4 | 99.3 | 98.0 |
| Example 3 | 99.6 | 99.6 | 99.4 | 99.3 | 98.3 |
| Comparative Example 6 | 99.6 | 99.6 | 99.4 | 99.3 | 97.6 |

As can be seen in Table 5 above, the contents of intact heavy chain and light in the formulations of Examples 1 to 3 after 4 weeks of storage at a temperature of 40° C. were 98.0% or more, which was higher than that of Comparative Example 6.

Oxidation Rate (Heavy-Chain Met 255)

TABLE 6

|  | After 0 week at 40 ± 2° C. | After 4 weeks at 40 ± 2° C. |
|---|---|---|
| Example 1 | 2.2 | 2.4 |
| Example 2 | 2.0 | 2.5 |
| Example 3 | 2.1 | 2.5 |
| Comparative Example 6 | 2.2 | 4.1 |

As can be seen in Table 6 above, the oxidation rates of heavy-chain Met 255 in the formulations of Examples 1 to 3 after 4 weeks of storage at a temperature of 40° C. were 2.5% or less, which was lower than that of Comparative Example 6.

Charge Variants (Acidic Peaks)

TABLE 7

|  | After 0 week at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|
| Example 1 | 20.5 | 20.5 | 20.5 | 27.0 | 33.5 |
| Example 2 | 20.6 | 20.8 | 20.6 | 27.9 | 34.5 |
| Example 3 | 20.3 | 20.9 | 20.8 | 27.5 | 34.4 |
| Comparative Example 6 | 20.4 | 20.9 | 20.9 | 30.3 | 38.6 |

As can be seen in Table 7, the acidic peaks of the formulations of Examples 1 to 3 after 4 weeks of storage at a temperature of 40° C. were 35% or less, which was lower than that of Comparative Example 6. It indicates that the formulations of Examples 1 to 3 are stable formulations in which deamidation that is a major cause of increasing acidic peaks less occurs.

Charge Variants (Basic Peaks)

TABLE 8

|  | After 0 week at 5 ± 3° C. | After 2 weeks at 5 ± 3° C. | After 4 weeks at 5 ± 3° C. | After 2 weeks at 40 ± 2° C. | After 4 weeks at 40 ± 2° C. |
|---|---|---|---|---|---|
| Example 1 | 40.6 | 40.1 | 40.2 | 37.4 | 34.4 |
| Example 2 | 40.5 | 39.8 | 39.8 | 36.3 | 33.1 |
| Example 3 | 40.4 | 39.6 | 39.8 | 36.5 | 33.3 |
| Comparative Example 6 | 40.4 | 39.8 | 40.0 | 35.1 | 30.9 |

As can be seen in Table 8 above, the basic peaks of the formulations of Examples 1 to 3 after 4 weeks of storage at a temperature of 40° C. were 33% or more, which was higher than that of Comparative Example 6.

Number of Sub-Visible Particles (≥1.00 μm, <100.00 μm)

TABLE 9

|  | After 0 week at 5 ± 3° C. | After 4 weeks at 5 ± 3° C. | After 4 weeks at 40 ± 2° C. |
|---|---|---|---|
| Example 1 | 1527 | 7645 | 7005 |
| Example 2 | 4405 | 14257 | 29500 |
| Example 3 | 4525 | 1493 | 26923 |
| Comparative Example 6 | 13282 | 6688 | 2319386 |

As can be seen in Table 9, the number of sub-visible particles (≥1.00 μm, <100.00 μm) in the formulations of Examples 1 to 3 after 4 weeks of storage at a temperature of 40° C. was 30,000 or less, which was smaller than that of Comparative Example 6.

Experimental Example 2

Effect of Amino Acid

For preparation of liquid pharmaceutical formulations to be used in Experimental Example 2, a buffer comprising sodium acetate was prepared so as to have a desired pH, and sorbitol was added thereto. Then, an antibody was added thereto and a surfactant and amino acid/taurine were added, thereby preparing the samples shown in Table 10 below. The concentration of each component is shown in Table 10 below. The concentration of the buffer means the concentration of acetate anion. The total volume was 1 ml.

TABLE 10

|  | Antibody content (mg/ml) | Surfactant | Sugar alcohol or NaCl | Buffer | pH | Amino acid/ taurine[1] |
|---|---|---|---|---|---|---|
| Example 1 | 100 | Polysorbate 80 0.05%(w/v) | Sorbitol 5%(w/v) | Sodium acetate 10 mM | 4.0 | — |
| Reference Example 1 | 100 | Polysorbate 80 0.05%(w/v) | Sorbitol 4%(w/v) | Sodium acetate 10 mM | 4.0 | L-alanine |
| Reference Example 2 | 100 | Polysorbate 80 0.05%(w/v) | Sorbitol 4%(w/v) | Sodium acetate 10 mM | 4.0 | L-asparagine |
| Reference Example 3 | 100 | Polysorbate 80 0.05%(w/v) | Sorbitol 4%(w/v) | Sodium acetate 10 mM | 4.0 | L-glutamine |
| Reference Example 4 | 100 | Polysorbate 80 0.05%(w/v) | Sorbitol 4%(w/v) | Sodium acetate 10 mM | 4.0 | L-glutamic acid |

TABLE 10-continued

| | Antibody content (mg/ml) | Surfactant | Sugar alcohol or NaCl | Buffer | Amino acid/ pH taurine[1] |
|---|---|---|---|---|---|
| Reference Example 5 | 100 | Polysorbate 80 0.05%(w/v) | Sorbitol 4%(w/v) | Sodium acetate 10 mM | 4.0 L-glycine |
| Reference Example 6 | 100 | Polysorbate 80 0.05%(w/v) | Sorbitol 4%(w/v) | Sodium acetate 10 mM | 4.0 L-isoleucine |
| Reference Example 7 | 100 | Polysorbate 80 0.05%(w/v) | Sorbitol 4%(w/v) | Sodium acetate 10 mM | 4.0 L-leucine |
| Reference Example 8 | 100 | Polysorbate 80 0.05%(w/v) | Sorbitol 4%(w/v) | Sodium acetate 10 mM | 4.0 L-methionine |
| Reference Example 9 | 100 | Polysorbate 80 0.05%(w/v) | Sorbitol 4%(w/v) | Sodium acetate 10 mM | 4.0 L-phenylalanine |
| Reference Example 10 | 100 | Polysorbate 80 0.05%(w/v) | Sorbitol 4%(w/v) | Sodium acetate 10 mM | 4.0 L-proline |
| Reference Example 11 | 100 | Polysorbate 80 0.05%(w/v) | Sorbitol 4%(w/v) | Sodium acetate 10 mM | 4.0 L-serine |
| Reference Example 12 | 100 | Polysorbate 80 0.05%(w/v) | Sorbitol 4%(w/v) | Sodium acetate 10 mM | 4.0 L-threonine |
| Reference Example 13 | 100 | Polysorbate 80 0.05%(w/v) | Sorbitol 4%(w/v) | Sodium acetate 10 mM | 4.0 L-tryptophan |
| Reference Example 14 | 100 | Polysorbate 80 0.05%(w/v) | Sorbitol 4%(w/v) | Sodium acetate 10 mM | 4.0 L-tyrosine |
| Reference Example 15 | 100 | Polysorbate 80 0.05%(w/v) | Sorbitol 4%(w/v) | Sodium acetate 10 mM | 4.0 Valine |
| Reference Example 16 | 100 | Polysorbate 80 0.05%(w/v) | Sorbitol 4%(w/v) | Sodium acetate 10 mM | 4.0 Taurine |
| Comparative Example 9 | 100 | Polysorbate 80 0.05%(w/v) | Sorbitol 4%(w/v) | Sodium acetate 10 mM | 4.0 L-aspartic acid |
| Comparative Example 10 | 100 | Polysorbate 80 0.05%(w/v) | Sorbitol 4%(w/v) | Sodium acetate 10 mM | 4.0 L-histidine |
| Comparative Example 11 | 100 | Polysorbate 80 0.05%(w/v) | Sorbitol 4%(w/v) | Sodium acetate 10 mM | 4.0 L-lysine |
| Comparative Example 12 | 100 | Polysorbate 80 0.05%(w/v) | Sorbitol 4%(w/v) | Sodium acetate 10 mM | 4.0 L-arginine |

[1] Amino acid or taurine was added in an amount of 5% (w/v) or less.

The formulations of Comparative Examples 9, 10, 11 and 12, containing aspartic acid, histidine, lysine and arginine, respectively, became solid after 24 hours of storage at 50±2° C.

For the formulations containing other amino acids or taurine, the stabilities after 24 hours of storage at 5±3° C. and 50±2° C. were measured, but there was no significant difference between these formulations and between the these formulations and the formulation of Example 1.

Experimental Example 3

Protein Concentration; Surfactant Concentration; and the Kind of Sugar

For preparation of liquid pharmaceutical formulations to be used in Experimental Example 3, a buffer comprising sodium acetate was prepared so as to have a desired pH, and sorbitol, mannitol, trehalose or sucrose was added thereto. Then, an antibody was added thereto and a surfactant was added, thereby preparing the samples shown in Table 11 below. The content of each component is shown in Table 11 below. The concentration of the buffer means the concentration of acetate anion. The total volume was 1 ml.

TABLE 11

| | Antibody content (mg/ml) | Surfactant | Sugar | Buffer | pH |
|---|---|---|---|---|---|
| Example 4 | 125 | Polysorbate 80 0.05%(w/v) | Sorbitol 5%(w/v) | Sodium acetate 10 mM | 5.0 |
| Example 5 | 110 | Polysorbate 80 0.05%(w/v) | Sorbitol 5%(w/v) | Sodium acetate 10 mM | 5.0 |
| Example 6 | 90 | Polysorbate 80 0.05%(w/v) | Sorbitol 5%(w/v) | Sodium acetate 10 mM | 5.0 |

TABLE 11-continued

|  | Antibody content (mg/ml) | Surfactant | Sugar | Buffer | pH |
|---|---|---|---|---|---|
| Example 7 | 145 | Polysorbate 80 0.05%(w/v) | Sorbitol 5%(w/v) | Sodium acetate 10 mM | 5.0 |
| Example 8 | 110 | Polysorbate 80 0.02%(w/v) | Sorbitol 5%(w/v) | Sodium acetate 10 mM | 5.0 |
| Example 9 | 110 | Polysorbate 80 0.1%(w/v) | Sorbitol 5%(w/v) | Sodium acetate 10 mM | 5.0 |
| Example 10 | 110 | Polysorbate 80 0.05%(w/v) | Mannitol 5%(w/v) | Sodium acetate 10 mM | 5.0 |
| Example 11 | 110 | Polysorbate 80 0.05%(w/v) | Trehalose 10%(w/v) | Sodium acetate 10 mM | 5.0 |
| Example 12 | 110 | Polysorbate 80 0.05%(w/v) | Sucrose 10%(w/v) | Sodium acetate 10 mM | 5.0 |

The formulations were measured for their stabilities after 0, 2 and 4 weeks of storage at a temperature of 5±3° C. and for their stabilities after 2 and 4 weeks of storage at a temperature of 40±2° C. and a relative humidity of 75±5%. The results of the measurement are shown in Tables 12 to 17 below.

Protein Concentration
Content of High-Molecular-Weight Components

TABLE 12

|  | Antibody content (mg/ml) | After 0 week | After 2 weeks at 5° C. | After 4 weeks at 5° C. | After 2 weeks at 40° C. | After 4 weeks at 40° C. |
|---|---|---|---|---|---|---|
| Example 6 | 90 | 1.0 | 1.1 | 1.1 | 0.8 | 0.8 |
| Example 5 | 110 | 1.1 | 1.1 | 1.2 | 1.0 | 1.0 |
| Example 4 | 125 | 1.1 | 1.2 | 1.2 | 1.2 | 1.2 |
| Example 7 | 145 | 1.2 | 1.2 | 1.3 | 1.3 | 1.3 |

As can be seen in Table 12 above, the high-molecular-weight component content increased as the antibody concentration increased. However, at an antibody concentration ranging from 90 to 145 mg/ml, the high-molecular-weight component contents after 4 weeks of storage at 5° C. and 40° C. were generally low.

Surfactant Concentration
Number of Sub-Visible Particles (≥1.00 μm, <100.00 μm)

TABLE 13

|  | Surfactant | After 0 week | After 2 weeks at 40° C. | After 4 weeks at 40° C. |
|---|---|---|---|---|
| Example 8 | Polysorbate 80 0.02%(w/v) | 590 | 9235 | 5581 |
| Example 5 | Polysorbate 80 0.05%(w/v) | 6076 | 3957 | 6458 |
| Example 9 | Polysorbate 80 0.1%(w/v) | 997 | 2678 | 1672 |

As can be seen in Table 13 above, at a surfactant concentration ranging from 0.02 to 0.1% (w/v), the number of sub-visible particles (≥1.00 μm, <100.00 μm) after 4 weeks of storage at 40° C. was 10,000 or less.

The Kind of Sugar
Content of a Main Component (Main Peak)

TABLE 14

|  | Sugar | After 0 week | After 2 weeks at 40° C. | After 4 weeks at 40° C. |
|---|---|---|---|---|
| Example 5 | Sorbitol 5%(w/v) | 98.9 | 98.5 | 98.1 |
| Example 10 | Mannitol 5%(w/v) | 98.9 | 98.6 | 98.2 |
| Example 11 | Trehalose 10%(w/v) | 98.9 | 98.6 | 98.2 |
| Example 12 | Sucrose 10%(w/v) | 98.9 | 98.6 | 98.1 |

As can be seen in Table 14 above, the formulations containing sorbitol, mannitol, trehalose or sucrose as a sugar showed a main component content of 98% or more after 4 weeks of storage at 40° C.

Charge Variants (Acidic Peaks)

TABLE 15

|  | Sugar | After 0 week | After 2 weeks at 40° C. | After 4 weeks at 40° C. |
|---|---|---|---|---|
| Example 5 | Sorbitol 5%(w/v) | 19.6 | 27.2 | 33.9 |
| Example 10 | Mannitol 5%(w/v) | 19.7 | 27.2 | 33.7 |
| Example 11 | Trehalose 10%(w/v) | 19.6 | 27.3 | 34.0 |
| Example 12 | Sucrose 10%(w/v) | 19.7 | 27.3 | 33.8 |

As can be seen in Table 15 above, the formulations containing sorbitol, mannitol, trehalose or sucrose as a sugar showed an acidic peak of 35% or less after 4 weeks of storage at 40° C.

Number of Sub-Visible Particles (≥1.00 μm, <100.00 μm)

TABLE 16

|  | Sugar | After 0 week | After 2 weeks at 40° C. | After 4 weeks at 40° C. |
|---|---|---|---|---|
| Example 5 | Sorbitol 5%(w/v) | 6076 | 3957 | 6458 |

TABLE 16-continued

|  | Sugar | After 0 week | After 2 weeks at 40° C. | After 4 weeks at 40° C. |
|---|---|---|---|---|
| Example 10 | Mannitol 5%(w/v) | 1055 | 865 | 4595 |
| Example 11 | Trehalose 10%(w/v) | 2803 | 1572 | 3554 |
| Example 12 | Sucrose 10%(w/v) | 1246 | 2416 | 11230 |

Number of Sub-Visible Particles (≥10.00 μm, <100.00 μm)

TABLE 17

|  | Sugar | After 0 week | After 2 weeks at 40° C. | After 4 weeks at 40° C. |
|---|---|---|---|---|
| Example 5 | Sorbitol 5%(w/v) | 128 | 11 | 115 |
| Example 10 | Mannitol 5%(w/v) | 36 | 37 | 84 |
| Example 11 | Trehalose 10%(w/v) | 42 | 13 | 56 |
| Example 12 | Sucrose 10%(w/v) | 40 | 42 | 118 |

As can be seen in Tables 16 and 17 above, in the formulations containing sorbitol, mannitol, trehalose or sucrose as a sugar, the number of sub-visible particles (≥1.00 μm, <100.00 μm) after 4 weeks of storage at 40° C. was 15,000 or less, and the number of sub-visible particles (≥10.00 μm, <100.00 μm) after 4 weeks of storage at 40° C. was 200 or less.

Experimental Example 4

The Kind of Surfactant and the Effect of Chelating Agent

For preparation of liquid pharmaceutical formulations to be used in Experimental Example 4, a buffer comprising sodium acetate was prepared so as to have a desired pH, and sorbitol was added thereto. Then, an antibody was added thereto and a surfactant or a mixture of a surfactant and a chelating agent was added, thereby preparing the samples shown in Table 18 below. The content of each component is shown in Table 18 below. The concentration of the buffer means the concentration of acetate anion. The total volume was 1 ml.

TABLE 18

|  | Antibody content (mg/ml) | Surfactant | Sugar | Buffer | pH | Chelating agent (EDTA) |
|---|---|---|---|---|---|---|
| Example 13 | 120 | Polysorbate 80 0.05%(w/v) | Sorbitol 5%(w/v) | Sodium acetate 10 mM | 5.0 | — |
| Example 14 | 120 | Polysorbate 20 0.05%(w/v) | Sorbitol 5%(w/v) | Sodium acetate 10 mM | 5.0 | — |
| Example 15 | 120 | Poloxamer 188 0.8%(w/v) | Sorbitol 5%(w/v) | Sodium acetate 10 mM | 5.0 | — |
| Comparative Example 13 | 120 | Polysorbate 80 0.05%(w/v) | Sorbitol 5%(w/v) | Sodium acetate 10 mM | 5.0 | 0.05 mg/ml |
| Comparative Example 14 | 120 | Polysorbate 20 0.05%(w/v) | Sorbitol 5%(w/v) | Sodium acetate 10 mM | 5.0 | 0.05 mg/ml |
| Comparative Example 15 | 120 | Poloxamer 188 0.8%(w/v) | Sorbitol 5%(w/v) | Sodium acetate 10 mM | 5.0 | 0.05 mg/ml |

The formulations shown in Table 18 above were measured for their stabilities after 0, 3 and 6 weeks of storage at a temperature of 5±3° C., a temperature of 25±2° C. and a relative temperature of 60±5%, and a temperature of 40±2° C. and a relative humidity of 75±5% under a closed condition. The results of the measurement are shown in Tables 19 and 20 below.

The Kind of Surfactant

Number of Sub-Visible Particles (≥10.00 μm, <100.00 μm)

TABLE 19

|  | Surfactant | After 0 week at 5° C. | After 3 weeks at 5° C. | After 6 weeks at 5° C. | After 3 weeks at 25° C. | After 6 weeks at 25° C. | After 3 weeks at 40° C. | After 6 weeks at 40° C. |
|---|---|---|---|---|---|---|---|---|
| Example 13 | Polysorbate 80 0.05%(w/v) | 50 | 149 | 46 | 34 | 182 | 249 | 55 |
| Example 14 | Polysorbate 20 0.05%(w/v) | 581 | 309 | 103 | 54 | 90 | 185 | 279 |
| Example 15 | Poloxamer 188 0.8%(w/v) | 208 | 67 | 86 | 172 | 56 | 344 | 2050 |

As can be seen in Table 19 above, in the formulation of Example 13, containing polysorbate 80 as a surfactant, the number of sub-visible particles (≥10.00 μm, <100.00 μm) after 6 weeks of storage at 40° C. was 100 or less (the smallest), and in the formulation of Example 15, containing poloxamer 188 as a surfactant, the number of sub-visible particles (≥10.00 μm, <100.00 μm) after 6 weeks of storage at 40° C. was 2,000 or more (the largest).

Effect of Chelating Agent (EDTA)

Oxidation Rate (Heavy-Chain Met 255)

TABLE 20

|  | Chelating agent (EDTA) | After 0 week at 5° C. | After 3 weeks at 5° C. | After 6 weeks at 5° C. | After 3 weeks at 40° C. | After 6 weeks at 40° C. |
|---|---|---|---|---|---|---|
| Example 13 | — | 1.9 | 1.9 | 1.9 | 2.3 | 2.5 |
| Example 14 | — | 2.0 | 1.9 | 1.9 | 2.2 | 2.4 |
| Example 15 | — | 1.9 | 1.9 | 1.9 | 2.3 | 2.5 |
| Comparative Example 13 | 0.05 mg/ml | 1.9 | 1.8 | 1.8 | 2.9 | 3.3 |
| Comparative Example 14 | 0.05 mg/ml | 2.3 | 1.8 | 2.0 | 2.8 | 3.3 |
| Comparative Example 15 | 0.05 mg/ml | 1.8 | 1.9 | 1.9 | 2.8 | 3.4 |

As can be seen in Table 20 above, in the formulations of Comparative Examples 13 to 15, containing a chelating agent (EDTA), the oxidation rate of heavy-chain Met 255 after 6 weeks of storage at 40° C. increased compared to that in the formulations of Examples 13 to 15, containing no chelating agent (EDTA).

Experimental Example 5

Long-Term Stability

For preparation of a liquid pharmaceutical formulation to be used in Experimental Example 5, a buffer comprising sodium acetate was prepared so as to have a pH of 5.0, and sorbitol was added thereto. Then, an antibody was added thereto and a surfactant was added, thereby preparing the sample shown in Table 21 below. The content of each component is shown in Table 21 below. The concentration of the buffer means the concentration of acetate anion. The total volume was 1 ml.

TABLE 21

| | Antibody content (mg/ml) | Surfactant | Sugar | Buffer | pH |
|---|---|---|---|---|---|
| Example 16 | 120 | Polysorbate 80 0.05%(w/v) | Sorbitol 5%(w/v) | Sodium acetate 25 mM | 5.0 |

The formulation shown in Table 21 was measured for its stability after 0, 3 and 6 months of storage at a temperature of 5±3° C. under a closed condition. The results of the measurement are shown in Tables 22 to 27 below.

Number of Sub-Visible Particles (≥10.00 μm, <400.00 μm)

TABLE 22

| | After 0 month at 5° C. | After 3 months at 5° C. | After 6 months at 5° C. | After 9 months at 5° C. | After 12 months at 5° C. |
|---|---|---|---|---|---|
| Example 16 | 35 | 26 | 48 | 32 | 43 |

As can be seen in Table 22 above, the number of sub-visible particles (≥10.00 μm, <400.00 μm) in the formulation of Example 16 after 12 months of storage at 5° C. was as small as 100 or less.

Content of Intact Immunoglobulin (Intact IgG %)

TABLE 23

| | After 0 month at 5° C. | After 3 months at 5° C. | After 6 months at 5° C. | After 9 months at 5° C. | After 12 months at 5° C. |
|---|---|---|---|---|---|
| Example 16 | 94.6 | 93.9 | 94.3 | 94.4 | 94.4 |

As can be seen in Table 23 above, the content of intact immunoglobulin G in the formulation of Example 16 after 12 months of storage at 5° C. was as high as 94% or more.

Content of intact heavy chain and light chain (Intact HC+LC %)

TABLE 24

| | After 0 month at 5° C. | After 3 months at 5° C. | After 6 months at 5° C. | After 9 months at 5° C. | After 12 months at 5° C. |
|---|---|---|---|---|---|
| Example 16 | 99.7 | 99.5 | 99.6 | 99.4 | 99.4 |

As can be seen in Table 24 above, the content of intact heavy chain and light chain in the formulation of Example 16 after 12 months of storage at 5° C. was as high as 99% or more.

Content of High-Molecular-Weight Components

TABLE 25

| | After 0 month at 5° C. | After 3 months at 5° C. | After 6 months at 5° C. | After 9 months at 5° C. | After 12 months at 5° C. |
|---|---|---|---|---|---|
| Example 16 | 0.5 | 0.9 | 0.9 | 0.8 | 0.7 |

As can be seen in Table 25 above, the content of high-molecular-weight components in the formulation of Example 16 after 12 months of storage at 5° C. was as low as 1.0% or less.

Content of Low-Molecular-Weight Components

TABLE 26

| | After 0 month at 5° C. | After 3 months at 5° C. | After 6 months at 5° C. | After 9 months at 5° C. | After 12 months at 5° C. |
|---|---|---|---|---|---|
| Example 16 | 0.0 | 0.1 | 0.1 | 0.1 | 0.3 |

As can be seen in Table 26 above, the content of low-molecular-weight components in the formulation of Example 16 after 12 months of storage at 5° C. was as low as 0.4% or less.

TNF-α Binding Affinity

TABLE 27

| | After 0 month at 5° C. | After 3 months at 5° C. | After 6 months at 5° C. | After 9 months at 5° C. | After 12 months at 5° C. |
|---|---|---|---|---|---|
| Example 16 | 95 | 98 | 116 | 101 | 97 |

As can be seen in Table 27 above, the TNF-α binding affinity of the formulation of Example 16 after 12 months of storage at 5° C. was as high as 95% or more.

The formulation of Example 16 was measured for its viscosity after 0, 0.5, 1, 2 and 3 months of storage at a temperature of 40±2° C. under a closed condition and for its viscosity after 6 months of storage at a temperature of 5±3° C. under a closed condition. The results of the measurement are shown in Table 28 below.

Viscosity (cP)

TABLE 28

| | After 0 month | After 0.5 months at 40° C. | After 1 month at 40° C. | After 6 months at 5° C. |
|---|---|---|---|---|
| Example 16 | 4.1 | 5.6 | 8.0 | 4.0 |

As can be seen in Table 28 above, the viscosity of the formulation of Example 16 was maintained at a low level (8.0 cp) after 1 month of storage at a temperature of 40° C.±2° C. and maintained at a low level (4.0 cp) after 6 months of storage at a temperature of 5° C.±3° C.

```
SEQUENCE LIST
SEQ ID NO. 1: Gln Phe Val Gly Ser Ser

SEQ ID NO. 2: Tyr Ala Ser

SEQ ID NO. 3: Gln Gln Ser His Ser Trp Pro Phe Thr

SEQ ID NO. 4: Gly Phe Ile Phe Ser Asn His Trp
```

-continued

SEQ ID NO. 5: Ile Arg Ser Lys Ser Ile Asn Ser Ala Thr

SEQ ID NO. 6: Ser Arg Asn Tyr Tyr Gly Ser Thr Tyr Asp Tyr

SEQ ID NO. 7: Asp Ile Leu Leu Thr Gln Ser Pro Ala Ile Leu Ser Val Ser Pro Gly Glu Arg
Val Ser Phe Ser Cys Arg Ala Ser Gln Phe Val Gly Ser Ser Ile His Trp Tyr Gln Gln Arg Thr
Asn Gly Ser Pro Arg Leu Leu Ile Lys Tyr Ala Ser Glu Ser Met Ser Gly Ile Pro Ser Arg Phe
Ser Gly Ser Gly Ser Gly Thr Asp Phe Thr Leu Ser Ile Asn Thr Val Glu Ser Glu Asp Ile Ala
Asp Tyr Tyr Cys Gln Gln Ser His Ser Trp Pro Phe Thr Phe Gly Ser Gly Thr Asn Leu Glu
Val Lys

SEQ ID NO. 8: Glu Val Lys Leu Glu Glu Ser Gly Gly Gly Leu Val Gln Pro Gly Gly Ser
Met Lys Leu Ser Cys Val Ala Ser Gly Phe Ile Phe Ser Asn His Trp Met Asn Trp Val Arg
Gln Ser Pro Glu Lys Gly Leu Glu Trp Val Ala Glu Ile Arg Ser Lys Ser Ile Asn Ser Ala Thr
His Tyr Ala Glu Ser Val Lys Gly Arg Phe Thr Ile Ser Arg Asp Asp Ser Lys Ser Ala Val Tyr
Leu Gln Met Thr Asp Leu Arg Thr Glu Asp Thr Gly Val Tyr Tyr Cys Ser Arg Asn Tyr Tyr
Gly Ser Thr Tyr Asp Tyr Trp Gly Gln Gly Thr Thr Leu Thr Val Ser

SEQ ID NO. 9:
  1 Met Asp Phe Gln Val Gln Ile Ile Ser Phe Leu Leu Ile Ser Ala Ser Val Ile Met Ser
 21 Arg Gly Asp Ile Leu Leu Thr Gln Ser Pro Ala Ile Leu Ser Val Ser Pro Gly Glu Arg
 41 Val Ser Phe Ser Cys Arg Ala Ser Gln Phe Val Gly Ser Ser Ile His Trp Tyr Gln Gln
 61 Arg Thr Asn Gly Ser Pro Arg Leu Leu Ile Lys Tyr Ala Ser Glu Ser Met Ser Gly Ile
 81 Pro Ser Arg Phe Ser Gly Ser Gly Ser Gly Thr Asp Phe Thr Leu Ser Ile Asn Thr Val
101 Glu Ser Glu Asp Ile Ala Asp Tyr Tyr Cys Gln Gln Ser His Ser Trp Pro Phe Thr Phe
121 Gly Ser Gly Thr Asn Leu Glu Val Lys Arg Thr Val Ala Ala Pro Ser Val Phe Ile Phe
141 Pro Pro Ser Asp Glu Gln Leu Lys Ser Gly Thr Ala Ser Val Val Cys Leu Leu Asn Asn
161 Phe Tyr Pro Arg Glu Ala Lys Val Gln Trp Lys Val Asp Asn Ala Leu Gln Ser Gly Asn
181 Ser Gln Glu Ser Val Thr Glu Gln Asp Ser Lys Asp Ser Thr Tyr Ser Leu Ser Ser Thr
201 Leu Thr Leu Ser Lys Ala Asp Tyr Glu Lys His Lys Val Tyr Ala Cys Glu Val Thr His
221 Gln Gly Leu Ser Ser Pro Val Thr Lys Ser Phe Asn Arg Gly Glu Cys ***

SEQ ID NO: 10:
  1 Met Gly Trp Ser Leu Ile Leu Leu Phe Leu Val Ala Val Ala Thr Arg Val Leu Ser Glu
 21 Val Lys Leu Glu Glu Ser Gly Gly Gly Leu Val Gln Pro Gly Gly Ser Met Lys Leu Ser
 41 Cys Val Ala Ser Gly Phe Ile Phe Ser Asn His Trp Met Asn Trp Val Arg Gln Ser Pro
 61 Glu Lys Gly Leu Glu Trp Val Ala Glu Ile Arg Ser Lys Ser Ile Asn Ser Ala Thr His
 81 Tyr Ala Glu Ser Val Lys Gly Arg Phe Thr Ile Ser Arg Asp Asp Ser Lys Ser Ala Val
101 Tyr Leu Gln Met Thr Asp Leu Arg Thr Glu Asp Thr Gly Val Tyr Tyr Cys Ser Arg Asn
121 Tyr Tyr Gly Ser Thr Tyr Asp Tyr Trp Gly Gln Gly Thr Thr Leu Thr Val Ser Ser Ala
141 Ser Thr Lys Gly Pro Ser Val Phe Pro Leu Ala Pro Ser Ser Lys Ser Thr Ser Gly Gly
161 Thr Ala Ala Leu Gly Cys Leu Val Lys Asp Tyr Phe Pro Glu Pro Val Thr Val Ser Trp
181 Asn Ser Gly Ala Leu Thr Ser Gly Val His Thr Phe Pro Ala Val Leu Gln Ser Ser Gly
201 Leu Tyr Ser Leu Ser Ser Val Val Thr Val Pro Ser Ser Ser Leu Gly Thr Gln Thr Tyr
221 Ile Cys Asn Val Asn His Lys Pro Ser Asn Thr Lys Val Asp Lys Lys Val Glu Pro Lys
241 Ser Cys Asp Lys Thr His Thr Cys Pro Pro Cys Pro Ala Pro Glu Leu Leu Gly Gly Pro

```
261 Ser Val Phe Leu Phe Pro Pro Lys Pro Lys Asp Thr Leu Met Ile Ser Arg Thr Pro Glu

281 Val Thr Cys Val Val Val Asp Val Ser His Glu Asp Pro Glu Val Lys Phe Asn Trp Tyr

301 Val Asp Gly Val Glu Val His Asn Ala Lys Thr Lys Pro Arg Glu Glu Gln Tyr Asn Ser

321 Thr Tyr Arg Val Val Ser Val Leu Thr Val Leu His Gln Asp Trp Leu Asn Gly Lys Glu

341 Tyr Lys Cys Lys Val Ser Asn Lys Ala Leu Pro Ala Pro Ile Glu Lys Thr Ile Ser Lys

361 Ala Lys Gly Gln Pro Arg Glu Pro Gln Val Tyr Thr Leu Pro Pro Ser Arg Asp Glu Leu

381 Thr Lys Asn Gln Val Ser Leu Thr Cys Leu Val Lys Gly Phe Tyr Pro Ser Asp Ile Ala

401 Val Glu Trp Glu Ser Asn Gly Gln Pro Glu Asn Asn Tyr Lys Thr Thr Pro Pro Val Leu

421 Asp Ser Asp Gly Ser Phe Phe Leu Tyr Ser Lys Leu Thr Val Asp Lys Ser Arg Trp Gln

441 Gln Gly Asn Val Phe Ser Cys Ser Val Met His Glu Ala Leu His Asn His Tyr Thr Gln

461 Lys Ser Leu Ser Leu Ser Pro Gly Lys ***
```

What is claimed is:

1. A stable liquid pharmaceutical formulation, comprising:
   (A) 90 to 145 mg/ml of infliximab;
   (B) 0.02 to 0.1% (w/v) of a surfactant comprising polysorbate 80;
   (C) 1 to 10% (w/v) of a sugar comprising sorbitol; and
   (D) 1 to 50 mM of a buffer comprising sodium acetate.

2. The stable liquid pharmaceutical formulation of claim 1, wherein said formulation has a pH of 4.0 to 5.5.

3. The stable liquid pharmaceutical formulation of claim 1, wherein the formulation is free of aspartic acid, lysine, arginine, or mixtures thereof.

4. The stable liquid pharmaceutical formulation of claim 1, wherein the formulation is free of NaCl, KCl, NaF, KBr, NaBr, Na$_2$SO$_4$, NaSCN, K$_2$SO$_4$, or mixtures thereof.

5. The stable liquid pharmaceutical formulation of claim 1, wherein said formulation is free of a chelating agent.

6. The stable liquid pharmaceutical formulation of claim 1, wherein the formulation has a viscosity in the range of approximately 8 cP after 1 month of storage at 40° C.±2° C. or approximately 4 cP after 6 months of storage at 5° C.±3° C.

7. The formulation of claim 1, wherein said formulation further comprises Taurine.

8. The formulation of claim 1, wherein said formulation comprises 100 to 125 mg/ml of infliximab.

9. The formulation of claim 1, wherein said formulation comprises 0.02 to 0.05% (w/v) of a surfactant comprising polysorbate 80.

10. The formulation of claim 1, wherein said formulation comprises 4 to 5% (w/v) of a sugar comprising sorbitol.

11. The formulation of claim 1, wherein said formulation comprises 10 to 25 mM of a buffer comprising sodium acetate.

12. A pre-filled syringe filled with the stable liquid pharmaceutical formulation of claim 1.

13. An auto-injector comprising the pre-filled syringe of claim 12.

14. A kit comprising: a container comprising said formulation of claim 1 and instructions for administration of said formulation to a patient.

* * * * *